(12) United States Patent
Persson

(10) Patent No.: US 8,505,537 B2
(45) Date of Patent: Aug. 13, 2013

(54) BREATHING PROTECTOR

(75) Inventor: Jan-Ove Persson, Hoor (SE)

(73) Assignee: Atos Medical AB (SE)

( * ) Notice: Subject to any disclaimer, the term of this patent is extended or adjusted under 35 U.S.C. 154(b) by 766 days.

(21) Appl. No.: 12/598,344

(22) PCT Filed: Apr. 30, 2008

(86) PCT No.: PCT/EP2008/055295
§ 371 (c)(1),
(2), (4) Date: Apr. 26, 2010

(87) PCT Pub. No.: WO2008/132222
PCT Pub. Date: Nov. 6, 2008

(65) Prior Publication Data
US 2010/0288284 A1    Nov. 18, 2010

(30) Foreign Application Priority Data

Apr. 30, 2007    (SE) .................................... 0701039

(51) Int. Cl.
*A61M 11/00* (2006.01)
(52) U.S. Cl.
USPC ............................. 128/205.27; 128/207.14
(58) Field of Classification Search
USPC ............ 128/200.26, 207.14, 207.15, 207.16, 128/207.29, 205.27; 623/9
See application file for complete search history.

(56) References Cited

U.S. PATENT DOCUMENTS

| 4,582,058 A | * | 4/1986 | Depel et al. ............... 128/207.17 |
| 4,971,054 A | * | 11/1990 | Andersson et al. ...... 128/207.16 |
| 5,487,382 A | | 1/1996 | Bezicot |
| 5,666,950 A | | 9/1997 | Smith |
| 5,738,095 A | | 4/1998 | Persson |
| 6,668,831 B1 | * | 12/2003 | Hegwood ................. 128/207.14 |
| 7,370,654 B2 | * | 5/2008 | Persson ..................... 128/207.16 |
| 2003/0029456 A1 | | 2/2003 | Lambert |

FOREIGN PATENT DOCUMENTS

| EP | 0861671 | 9/1998 |
| WO | WO-91/05579 | 5/1991 |
| WO | WO-99/60954 | 12/1999 |
| WO | WO-00/74602 | 12/2000 |
| WO | WO-2005/058403 | 6/2005 |

OTHER PUBLICATIONS

International Search Report for PCT/EP2008/055295.

* cited by examiner

*Primary Examiner* — Steven Douglas
(74) *Attorney, Agent, or Firm* — Rader, Fishman & Grauer PLLC

(57) ABSTRACT

A breathing protector for use in a stoma of a laryngectomized or tracheotomised person is provided. This breathing protector is provided with an inlet and an outlet, such that an air flow in use will pass from the surroundings of said person through said inlet to said outlet, into trachea of said person. The breathing protector further comprises a heat-moisture exchanger (3) and a bacteriological filter (4), such that said air flow will pass through said heat-moisture exchanger and said bacteriological filter when said air flow in use passes through said inlet to said outlet. Also, the breathing protector is provided with a closing member (6) that may be activated to close the communication between said at least one inlet and said at least one outlet.

23 Claims, 6 Drawing Sheets

BREATHING PROTECTOR

CROSS-REFERENCES TO RELATED APPLICATION

This application is a National Stage application which claims the benefit of International Application No. PCT/EP2008/055295, filed Apr. 30, 2008, which claims priority based on Sweden Patent Application No. 0701039-0, filed Apr. 30, 2007, both of which are hereby incorporated by reference in their entirety.

FIELD OF THE INVENTION

This invention pertains in general to the field of a breathing protector for use in a stoma of a laryngectomized or tracheotomised person, said breathing protector having at least one inlet and at least one outlet, such that an air flow in use will pass from the surroundings of said person through said inlet to said outlet, into trachea of said person, said breathing protector comprising a heat-moisture exchanger and a bacteriological filter, such that said air flow will pass through said heat-moisture exchanger and said bacteriological filter when said air flow in use passes through said inlet to said outlet.

BACKGROUND OF THE INVENTION

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air flow, can be closed to divert the airflow.

In this respect filter devices and breathing protectors have been developed to enable moisturizing of inhaled air and removal of small particles and bacteriological substances in said inhaled air. This is to resemble the functions of a nose. However, there are several complications related to the manufacturing of such devices. Firstly, the user of such devices is in need of good moisturizing and removal effect while keeping the size, such as the surface area, of the device as small as possible. Secondly, the moisturizing effect and removal effect is in need of large surface area, while not creating a too large resistance over the device. These criterions are contradictive, which the observant reader already has acknowledged. Also, a person with a laryngectomy has to hold his finger or thumb over these devices when wishing to speak, to thereby obstruct the air flow through the device and the stoma through the tracheal wall, which will burden the filter with undue contamination, due to transfer of impurities from the finger of the user to the filter.

U.S. Pat. No. 5,666,950 describes a device for filtering air that is to be breathed through a tracheostoma. This device comprises a pre-filter of electrostatically charged fibres, a first layer formed of activated carbon and a second layer of a hydrophilic material. The use of activated carbon provides filtration of small particles and absorption of gases, with a limited increase in the resistance to airflow through the device. However, the finger or thumb of the user will influence the antibacterilogical effect of the bacteriological filter in a negative way, since it is unreasonable to demand a totally bacteriological free condition of said finger or thumb, which means that said filter will be contaminated by time. Furthermore, the device according to U.S. Pat. No. 5,666,950 does only achieve an antibacteriological effect of approximately 50%, since the surface area of the bacteriological filter is restricted to the surface area of the opening communicating with the surroundings, while providing an adequate resistance over the device.

U.S. Pat. No. 5,487,382 describes an artificial nose with a housing and a hydrophilic filtering disc, further comprising a cap, which can be moved up and down to open/close windows in the housing. The artificial nose according to U.S. Pat. No. 5,487,382 has to be actively moved from an open position to a closed position and vice versa, and has a very limited antibacteriological effect.

Hence, an improved breathing protector would be advantageous and in particular a breathing protector allowing for increased antibacteriological effect and an excellent moisturizing effect, while also providing the possibility to a patient to keep the breathing protector closed, such as during speech, without undue contamination of the filter by holding a finger or thumb over said opening during the entire period of speech. It would also be advantageous to obtain a breathing protector with an increased antibacteriological effect and the possibility for a patient to keep the breathing protector closed, such as during speech, without undue contamination of the filter by holding a finger or thumb over said opening, which breathing protector not is persued by having to be actively moved from an open position to a closed position and vice versa. It would also be advantageous to provide a breathing protector allowing for an increased antibacteriological effect and an excellent moisturizing effect, while still providing a small breathing protector with a satisfactory resistance over said breathing protector.

SUMMARY OF THE INVENTION

Accordingly, the present invention seeks to mitigate, alleviate or eliminate one or more of the above-identified deficiencies and to provide an improved breathing protector of the kind referred to. For this purpose the breathing protector is characterized by a closing member that may be activated to close the communication between said at least one inlet and said at least one outlet.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a breathing protector and in particular to a breathing protector for use in a stoma of a laryngectomized or tracheotomised person, where said stoma is communicating with trachea of said person. However, the invention is not limited to this application but may be applied to other technical fields in which one wishes to remove bacteriological matter from an air stream while also moisturizing said air stream and providing the possibility to close said air stream.

Figure 1:
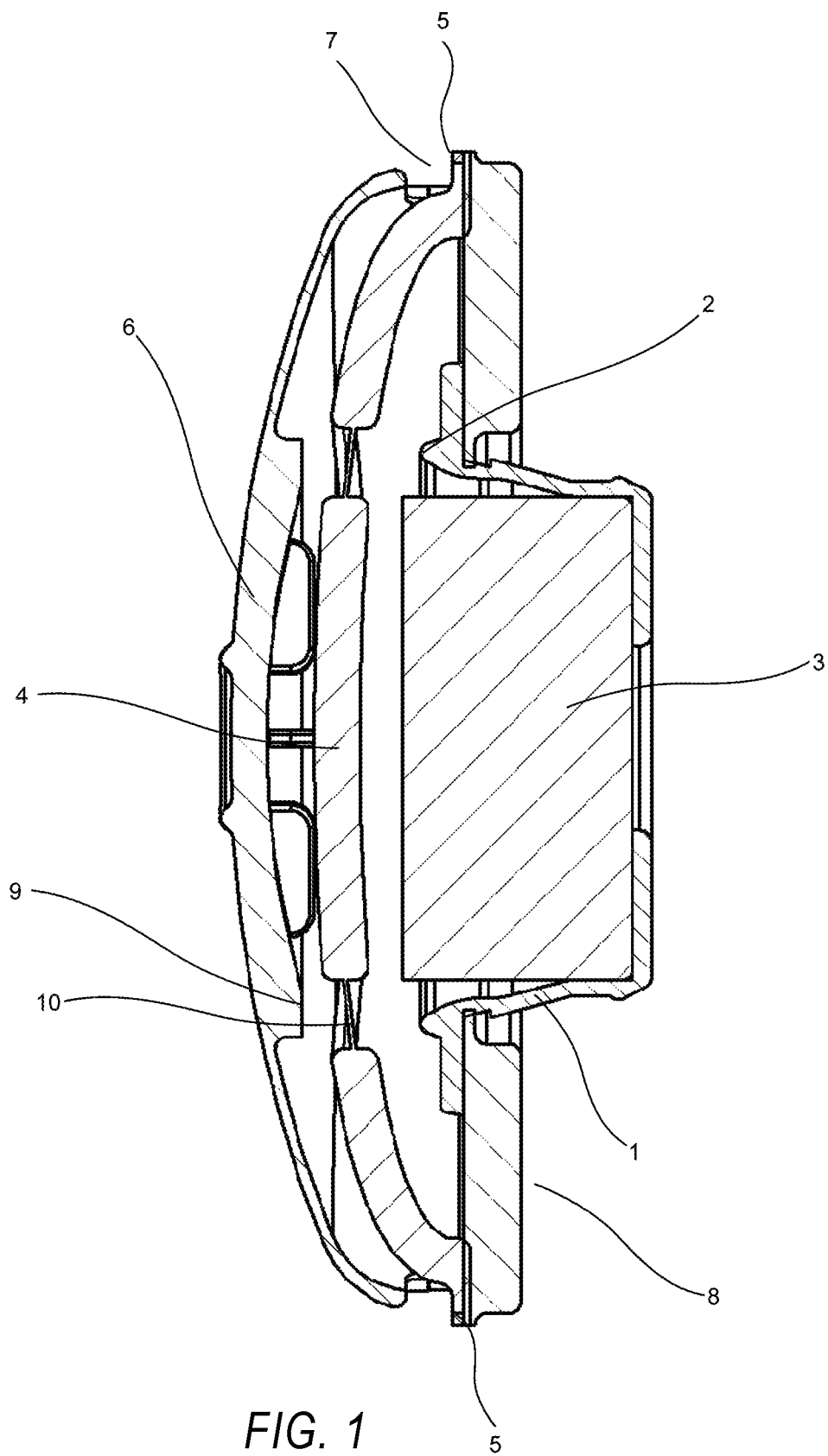
FIG. 1 is a cross sectional view of a breathing protector according to an embodiment of the present invention.
Figure 2:
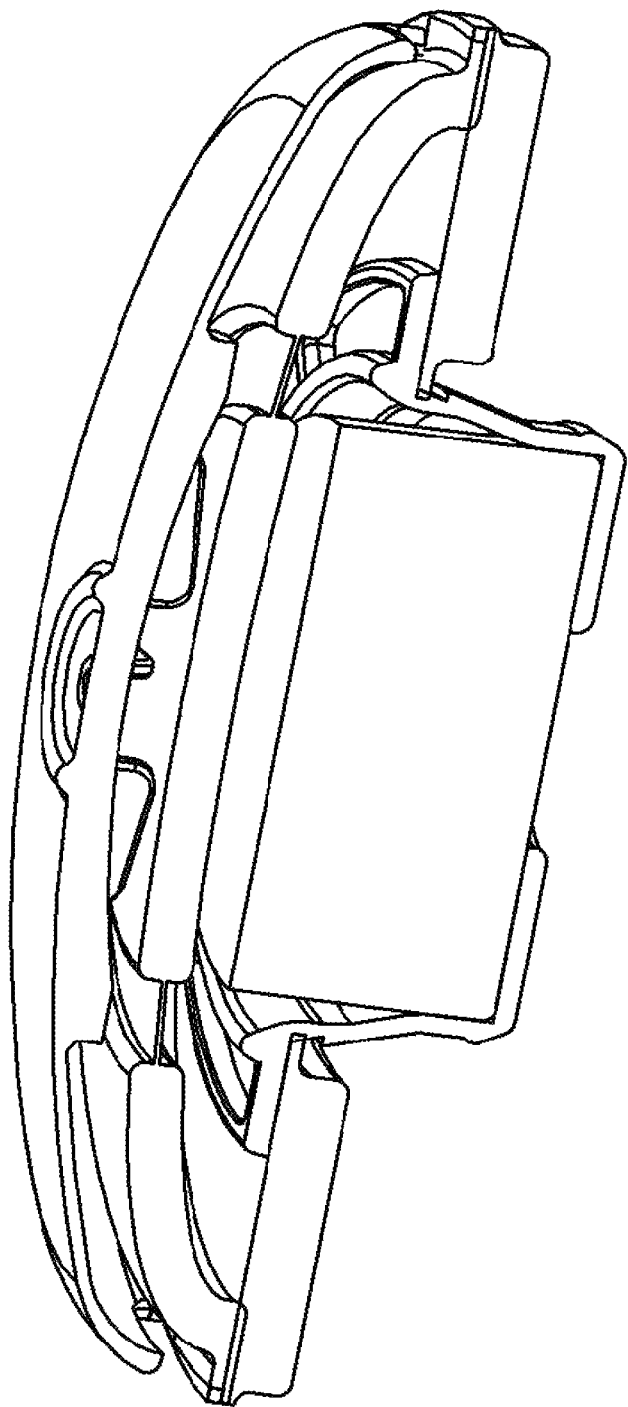
FIG. 2 is a perspective, cross sectional view of a breathing protector according to an embodiment of the present invention.

In an embodiment of the invention according to FIGS. 1 and 2 a breathing protector is provided. This breathing protector comprises a housing 1, with an accommodation, said housing 1 having a first and a second opening. The first opening of the housing 1 is provided with a closing surface 2, surrounding the first opening. This accommodation accommodates a heat-moisture exchanger 3, such that air passes through said heat-moisture exchanger when said air passes from said first opening to said second opening. A bacteriological filter 4 is applied on the breathing protector over the first opening. Thus, air passes through the bacteriological filer 4 and then the heat-moisture exchanger 3 when passing from the surroundings through the stoma, wherein or over which the breathing protector is arranged, into trachea of the patient through the second opening of the housing.

In one embodiment said closing surface 2 may be arranged as a closing rib, whereby the sealing action is performed by the connection area of the closing rib. This closing rib may have a smaller connection area than a surface with a greater breadth, whereby the closing force only has to act on a smaller area giving a higher sealing pressure.

The material of the heat-moisture exchanger should include flow passages therein, and should have an open structure in which the flow passages are randomly oriented. The material may comprise paper, foamed plastics, wadding made of different fibres, or combinations thereof. It may also be impregnated with a moisture absorbing substance. Furthermore, it is advantageous if the pores or interstices in the material do not have any special direction, such that the breathing air easily may pass through the material in a number of directions in order to achieve the intended deflection.

In one embodiment of the present invention the bacteriological filter 4 is an electrostatic filter.

The bacteriological filter 4, according to the embodiment disclosed in FIG. 1, is arranged in a multi-planar way in respect of the first opening. Thus, the bacteriological effect, provided by said bacteriological filter 4, is obtained in more than one plane. In this way the bacteriological effect may be obtained in a large surface area while still providing the possibility to keep the size of the breathing protector small. Thus, the breathing protector may be kept from being bulky to the person wearing the breathing protector, while still providing a maximum bacteriological effect. The term "multi-planar" is not intended to be limited to several sheets or layers, but is rather intended to illustrate a three-dimensional structure in contrast to a two-dimensional structure, such as a planar sheet or layer.

Thus, the thickness of such a planar sheet or layer is not intended to give a three-dimensional structure in this respect.

The bacteriological filter 4, according to the embodiment disclosed in FIGS. 1 and 2, is arranged in a multi-planar way in respect of the first opening by attaching the bacteriological filter 4 to a rim 5, which rim 5 has a larger circumference than the circumference of the first opening. This rim 5 may have a substantially circular or ring shape. Thus, the bacteriological filter 4 extends from the closing surface, such as the closing rib 2, to the rim 5, then covering the cross section area of the rim 5. The bacteriological filter 4 may thus be arranged to enclose the first opening of the housing 1, such that the bacteriological filter 4 will have a larger surface area than the area of the first opening of the housing 1. In this respect the term surface area is not intended to include porosity of the bacteriological filter 4, but merely the outer area of the bacteriological filter 4, i.e. the circumferential area of the bacteriological filter 4. Effective area is instead used to define the surface area including the porosity of the bacteriological filter 4. In this way the effective area of the bacteriological filter 4 may be increased by the multi planar structure without increasing the pressure drop over the bacteriological filter 4, while only being limited by the cross section area of the rim 5 in respect of the size of the breathing protector. This increase in effective area, while only being limited by the cross section area of the rim 5, provides an antibacteriological effect of more than 99%.

In another embodiment of the present invention the bacteriological filter is pleated, folded, curved, arched, or in other ways provided with a multi planar structure, to provide a maximized anti-bacteriological effect in a smaller size of the breathing protector.

Figure 3:
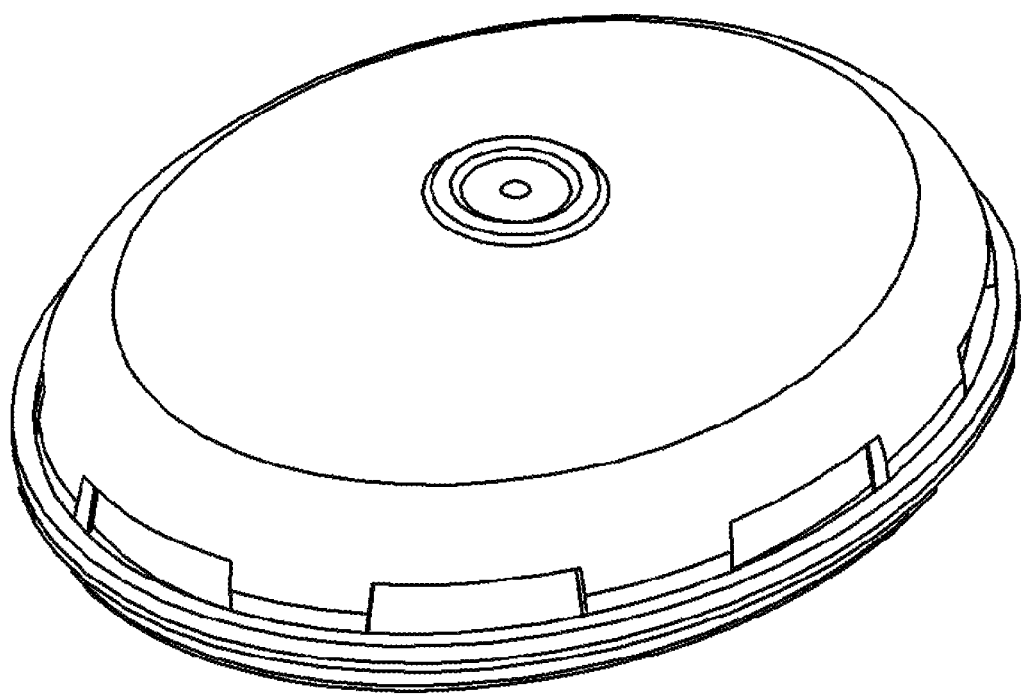
FIG. 3 is a perspective view of the side facing the surroundings of a breathing protector according to an embodiment of the present invention.
Figure 4:
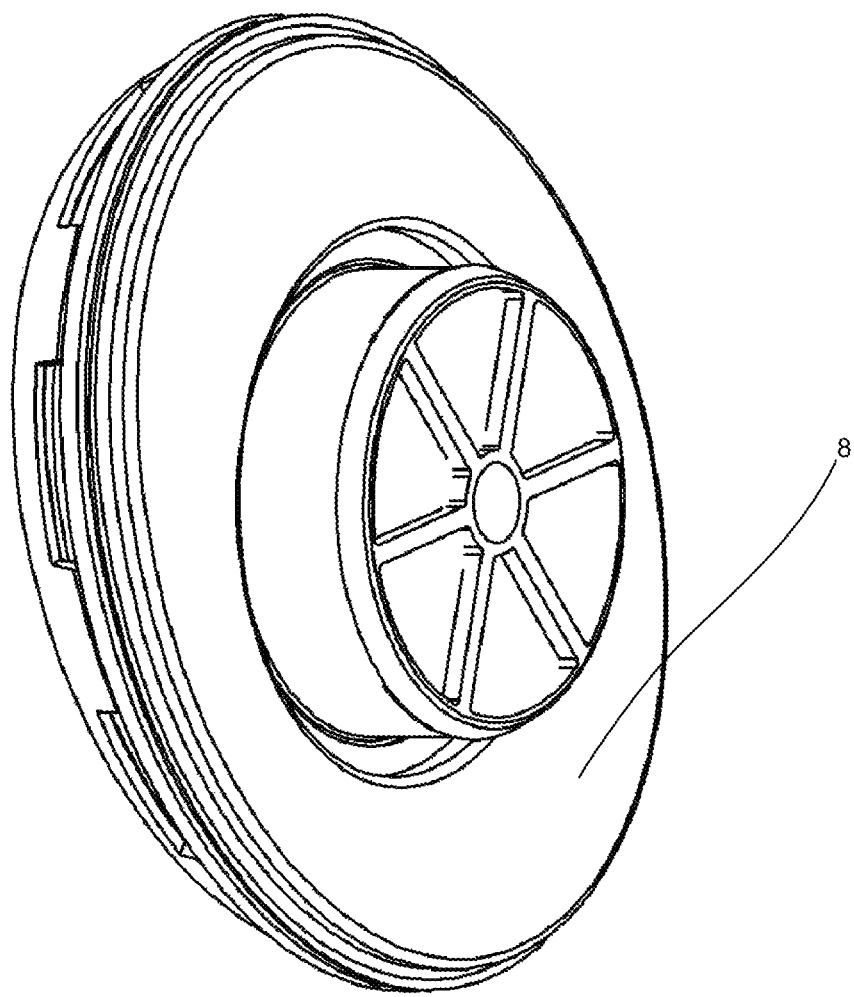
FIG. 4 is a perspective view of the side facing the patient of a breathing protector according to an embodiment of the present invention, FIG. 5 perspective, cross sectional view of a breathing protector according to an embodiment of the present invention.

In the embodiment according to FIG. 1, a flexible cover 6 is provided externally the bacteriological filter 4, which is attached to, or integrated with, the rim 5. Thus, the rim 5 may be the circumference of the flexible cover 6. The flexible cover 6 is arranged such that first inlets 7 are provided between the flexible cover 6 and the rim 5. Thus, said first inlets 7 are provided, through which air passes to thereafter get in contact with the bacteriological filter. Since the flexible cover 6 in this embodiment only is provided external of the bactertiological filter, which is illustrated in FIG. 3, across the rim 5, a second inlet 8 is provided facing the neck of the person wearing the breathing protector. This second inlet 8 is easy to derive from FIG. 4, which is a perspective view of the side facing the patient, according to one embodiment of the present invention. In this way a large surface area providing an antibacteriological effect may be obtained. Also, the second inlet 8 effects the air to bend around the rim 5 and makes the air to get in contact with the skin of the patient, whereby the turbulence of the air is increased and heat from the patients skin is transferred from to the air before the air is inhaled. Thus, the heating and moisturizing effects of the heat-moisture exchanger 3 may be somewhat increased. Also, the second inlet 8 facing the neck of the person wearing the breathing protector, further limits the risk of clothing obstructing the inlets of the breathing protector, since the inlets not only is directed parallel to the skin of the wearer, in form of the first inlet 7, but also towards the skin of the wearer, in form of the second inlet 8.

The resiliency of the flexible cover 6 allows the flexible cover 6 to be pressed down, inwardly, to closingly fit with the closing surface 2, such as the closing rib 2. A closing effect is obtained when the flexible cover 6 is pressed against the closing rib 2. In this respect the flexible cover 6 may be provided with an abutment 9 to facilitate the closure of the breathing protector. By achieving closing action from pressing down the flexible cover 6 instead of blocking airflow by holding a finger on the filter of the filter device, the bacteriological filter may be relieved from undue contamination from the finger. The closure of the breathing protector is affected to provide the patient with a faculty of speech. The resiliency of the flexible cover 6 further allows the flexible cover 6 to return to an open state of the breathing protector when pressure thereupon ceases. Thus, the user may press the flexible cover 6 to turn the breathing protector into a speaking mode/state, when the user wishes to speak, and simply release the pressure on the flexible cover 6 when the user wants to quit speaking and returning breathing protector into breathing mode/state.

In one embodiment of the present invention the bactertiological filter may be positioned in between the closing surface 2, such as the closing rib 2, and flexible cover 6, such that the bacteriological filter is compressed in between the closing rib 2 and the flexible cover 6 during closure of the breathing protector. This is disclosed in the embodiment according to FIGS. 1 and 2. To facilitate the closure of the breathing protector the bacteriological filter may be provided with an area 10, having a thinner thickness than the rest of the bacteriological filter, corresponding to the interaction area of the closing rib 2 and the flexible cover 6.

Figure 5:
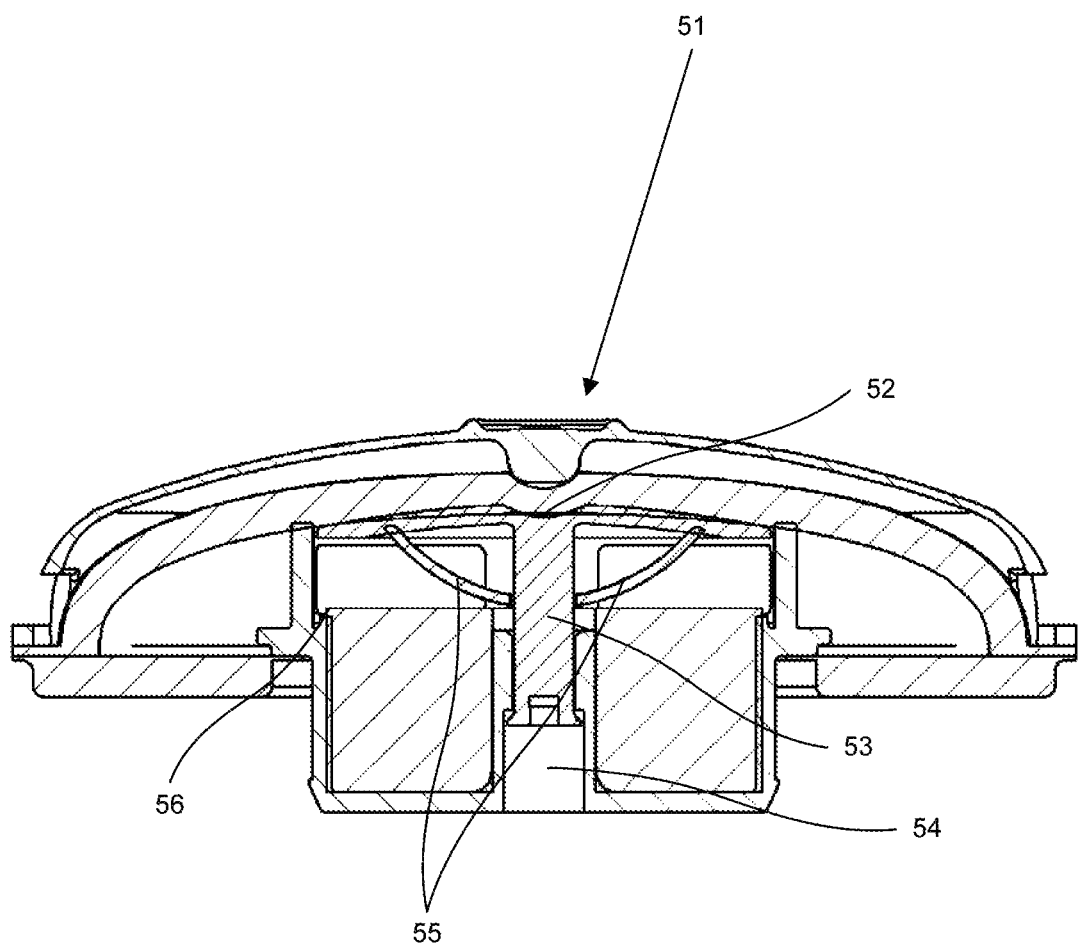

In another embodiment of the present invention the bacteriological filter is attached to the closing surface 2, such as the closing rib 2, such that the bacteriological filter is provided inside and outside the closing rib 2. In this embodiment the closing rib 2 and the flexible cover 6 may interact directly, without squeezing the bacteriological filter there between, to provide a closure of the breathing protector. In still one embodiment, according to FIG. 5, the breathing protector may be assembled by fitting a bacteriological filter around a housing, with an accommodation, having a first and a second opening, such housing being similar to the one illustrated in FIG. 1. The accommodation accommodates a heat-moisture exchanger, such that air passes through said heat-moisture exchanger when said air passes from said first opening to said second opening. The hole of the ring of bacteriological filter corresponds to the outer circumference of the housing, such that the ring of bacteriological filter may be closingly fitted around the housing. The fitting may be improved by attaching the ring to the housing by aid of an adhesive agent. In another embodiment the attachment of the ring to the housing may be performed by ultrasonic welding. Thereafter a patch of bacteriological filter, having a shape corresponding to the outer circumference of the ring may be applied and sealingly attached on top of the ring along the outer edge of the ring and the patch, such that air must pass through a bacteriological filter, i.e. either the ring or the patch, when air in use passes through the breathing protector. On top of the patch a closing lid may be attached, also along the outer edge of the ring and the patch. The closing lid may be provided with inlets along the outer edge, such that air may pass through these inlets and then through the patch of bacteriological filter, when air in use passes through the breathing protector. The lid ensures a minimized contamination of the bacteriological filter, thus prolonging the anti-bacteriological effect of the breathing protector, since the fingers of the user is prevented from coming in contact with the bacteriological filter.

The housing, comprising the heat-moisture exchanger, may be provided with a closing mechanism at the first opening, giving the effect that air-flow through the breathing protector is prevented when the closing mechanism is pressed towards the housing. Thus, when the user of the breathing protector presses on the closing lid, towards the housing, the user will activate the closing mechanism mounted on the housing, whereby air-flow through the breathing protector is prevented. This action may, as discussed above, be performed when the user wants to talk. This closing mechanism 51 is disclosed in FIG. 5, and may comprise a closing disc 52 and a stabilizing bar 53, said stabilizing bar running through the lumen of a tube 54 in the centre of the housing and the heat-moisture exchanger. The tube is connected to a web in the second opening of the housing, to thereby stabilizing the position of the tube in relation to the housing. The closing mechanism may also comprise a spring unit 55, connected to the closing disc 52, giving rise to an opening action when no force is applied on the breathing protector, such as the force applied by the user when the user wants to prevent air-flow through the breathing protector. This spring unit 55 may be an arched or curved flexible bar, extending from a first to a second point along the circumference of the closing disc, said first and second points being located substantially diagonally in respect of each other along said circumference. The arched or curved bar is also in contact, such as attached to or integrated with, the tube 54 at a distance from the closing disc 52, when the closing mechanism is in a resting position, i.e. when no force according to above is applied on the breathing protector. When a force is applied the arched or curved flexible bar allows the closing disc 52 to move along centre axis of the housing, until the circumference rests against a stop member 56. This stop member 56 may be a protrusion or protrusions arranged along the inner side of the housing. The resting of the closing disc 52 on the stop member 56 results in a sealing action, such that air-flow through the breathing protector is prevented. When the force is released the spring unit 55 moves the closing disc 52 along the centre axis of the housing in the opposite direction, thus releasing the closing action, whereby air-flow through the breathing protector again is obtained. The closing unit 51 may also comprise multiple arched or curved flexible bars, whereby the resiliency of the closing mechanism may be adjusted.

Figure 6:
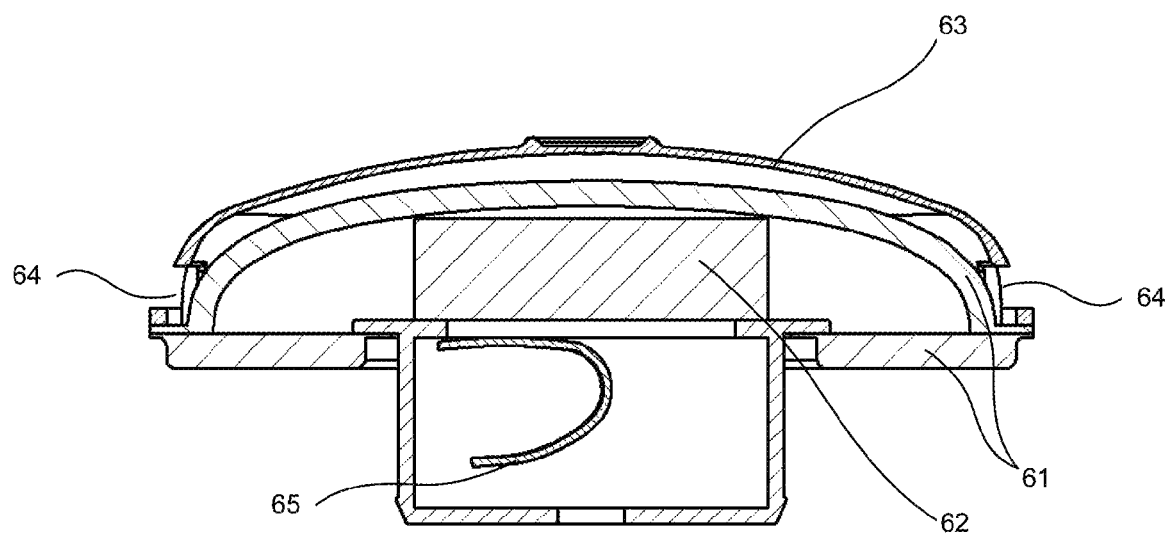
FIG. 6 is a cross sectional view of a breathing protector comprising a speech valve according to one embodiment of the present invention.

In still one embodiment, according to FIG. 6, the breathing protector may be assembled by fitting a bacteriological filter 61 on an automatic speech valve. A heat-moisture exchanger 62 is in this embodiment located in the flow path of the speech valve, such that inhaled air must pass through said heat-moisture exchanger 62. The hole of the ring of bacteriological filter corresponds to the outer circumference of the speech valve, such that the ring of bacteriological filter may be closingly fitted around the housing of the speech valve. The fitting may be improved by attaching the ring to the speech valve by aid of an adhesive agent. In another embodiment the attachment of the ring to the speech valve may be performed by ultrasonic welding. Thereafter a patch of bacteriological filter, having a shape corresponding to the outer circumference of the ring may be applied and sealingly attached on top of the ring along the outer edge of the ring and the patch, such that air must pass through a bacteriological filter, i.e. either the ring or the patch, when air in use passes through the breathing protector in form of a speech valve. On top of the patch a closing lid 63 may be attached, also along the outer edge of the ring and the patch. The closing lid 63 may be provided with inlets 64 along the outer edge, such that air may pass through these inlets and then through the patch of bacteriological filter, when air in use passes through this breathing protector with integrated speech valve. The automatic speech valve is in this context a speech valve provided with a flap 65, which during strong exhalation will close the air flow through the speech valve, and therefore also through the breathing protector. The function of an automatic speech valve of this kind is known to the skilled artisan.

In the embodiments described above, a breathing protector for use in a stoma of a laryngectomized or tracheotomised person has been described. This breathing protector is configured with at least one inlet and at least one outlet, such that an air flow in use will pass from the surroundings of said person through said inlet to said outlet, into trachea of said person. It is obvious to the skilled artisan, even if it has not been specifically disclosed, that the inlets and outlets may be divided into an increased amount by merely dividing the specific inlets and outlets already disclosed. Furthermore, this breathing protector comprises a heat-moisture exchanger 3 and a bacteriological filter 4, such that said air flow will pass through said heat-moisture exchanger and said bacteriological filter when said air flow in use passes through said inlet to said outlet. Also, the breathing protector, according to the disclosures above, comprises a closing member 6 that may be activated to close the communication between said at least one inlet and said at least one outlet. Even though the closing member disclosed in the embodiments above have been illustrated as a member of, or attached to, the flexible cover 6, the present inventor also envision that the closing member may be situated underneath the bacteriological filter, i.e. located after the bacteriological in the air flow path during inhaling. Such a closing member could be pressed or slid into interaction with the opening or inlet of the breathing protector, to thereby close the communication between said at least one inlet and said at least one outlet. This embodiment is also incorporated in the present invention, even though the bacteriological filter would be rendered contaminated by the contact with the hand of the user, during activation.

The elements and components of the embodiments of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A breathing protector for use in a stoma of a laryngectomized or tracheotomised person, said breathing protector having at least one inlet and at least one outlet, such that an air flow in use will pass from the surroundings of said person through said inlet to said outlet, into trachea of said person, said breathing protector comprising:
   a heat-moisture exchanger and a bacteriological filter, such that said air flow will pass through said heat-moisture exchanger and said bacteriological filter when said air flow in use passes through said at least one inlet, to said at least one outlet,
   a closing member selectively activated to close the communication between said at least one inlet and said at least one outlet, and
   a flexible cover.

2. The breathing protector according to claim 1, wherein said bacteriological filter is arranged multi planar, such that an antibacteriological effect is obtained in more than one plane.

3. The breathing protector according to claim 2, wherein said bacteriological filter is at least one of pleated, folded, curved, and arched, such that a multi planar structure is provided.

4. The breathing protector according to claim 1, wherein said heat-moisture exchanger is arranged in a housing provided with a first opening and said at least one outlet.

5. The breathing protector according to claim 4, wherein said housing is provided with a closing surface at said first opening, when selectively activated said closing member cooperates with said closing surface to close the communication between said at least one inlet and said at least one outlet.

6. The breathing protector according to claim 5, wherein said bacteriological filter is attached to said closing surface.

7. The breathing protector according to claim 5, wherein said bacteriological filter is arranged to be compressed in an interaction area between said closing member and said closing surface when closing said communication.

8. The breathing protector according to claim 7, wherein said bacteriological filter is provided with an area having a thinner thickness than the rest of the bacteriological filter, said area corresponding to the interaction area in between said closing surface and said closing member.

9. The breathing protector according to claim 4, comprising a rim, said rim having a larger circumference than said first opening, said bacteriological filter being attached to said rim, such that said bacteriological filter extends from said closing surface to said rim, whereby at least one inlet is provided between said closing surface and said rim, and said bacteriological filter covers a cross sectional area of said rim, whereby said bacteriological filter is arranged in a multi-planar way.

10. The breathing protector according to claim 1, wherein said flexible cover is external to said bacteriological filter and is attached to said rim.

11. The breathing protector according to claim 10, wherein said at least one inlet is provided between said flexible cover and said rim.

12. The breathing protector according to claim 1, wherein said flexible cover is said closing member.

13. The breathing protector according to claim 12, wherein said flexible cover is provided with an abutment shaped to fit against said closing surface to facilitate the closure of said breathing protector, wherein said closing surface is a closing rib.

14. The breathing protector according to claim 1, wherein said closing member comprises a closing disc and a stabilizing bar said stabilizing bar running through a lumen of a tube running through said breathing protector.

15. The breathing protector according to claim 14, wherein said tube is connected to a web at said at least one outlet.

16. The breathing protector according to claim 14 wherein said closing member comprises a spring unit connected to said closing disc.

17. The breathing protector according to claim 16, wherein said spring unit is at least one of an arched and curved flexible bar extending from a first point to a second point along a circumference of said closing disc, said first and second points being located substantially diagonally in respect of each other along said circumference, and said spring unit is at least, one of attached to and integrated with said tube at a distance from said closing disc, when said closing mechanism is in a resting position.

18. The breathing protector according to claim 14, comprising a stop member arranged along an inner side of said breathing protector, such that said closing disc may provide a sealing action when resting on said stop member.

19. The breathing protector according to claim 17, wherein said spring unit comprises multiple flexible bars, said flexible bars being at least one of arched and curved.

20. The breathing protector according to claim 1, comprising an automatic speech valve.

21. A breathing protector for use in a stoma of a laryngectomized or tracheotomised person, said breathing protector having a housing with at least a first opening and at least a second opening, such that an air flow in use will pass from the surroundings of said person through said first opening to said second opening, into trachea of said person, said breathing protector comprising:
a heat-moisture exchanger and a bacteriological filter, such that said air flow will pass through said heat-moisture exchanger and said bacteriological filter when said air flow in use passes through said first opening to said second opening, and
a rim having a larger circumference than a circumference of said first opening, said bacteriological filter extending from said housing to said rim and covering a cross sectional area of said rim, such that air flow in use will pass from the surroundings of said person through said bacteriological filter before said first opening.

22. The breathing protector according to claim 21, comprising a cover external to said bacteriological filter, and being at least one of attached and integrated with said rim.

23. A method for closing a breathing protector for use in a stoma of a laryngectomized or tracheotomised person, said breathing protector having a housing with at least a first opening and at least a second opening, such that an air flow in use will pass from the surroundings of said person through said first opening to said second opening, into trachea of said person, said breathing protector comprising a heat-moisture exchanger and a bacteriological filter, said bacteriological filter enclosing said first opening, such that said air flow will pass through said heat-moisture exchanger and said bacteriological filter when said air flow in use passes through said first opening to said second opening, said breathing protector further comprising a flexible cover external to said bacteriological filter, and
closing said, first opening by pressing said cover onto said bacteriological filter.

* * * * *